United States Patent [19]
Van Der Merwe

[11] Patent Number: 5,318,537
[45] Date of Patent: Jun. 7, 1994

[54] SYRINGE

[75] Inventor: Marius Van Der Merwe, Cape Province, South Africa

[73] Assignee: Van Der Merwe Corporation, Chicago, Ill.

[21] Appl. No.: 866,974

[22] Filed: Apr. 10, 1992

[30] Foreign Application Priority Data

Apr. 13, 1991 [GB] United Kingdom ................ 9107910
Jun. 27, 1991 [GB] United Kingdom ................ 9113821

[51] Int. Cl.$^5$ .............................................. A61M 5/00
[52] U.S. Cl. ................................... 604/110; 604/218; 604/228
[58] Field of Search ............... 604/110, 218, 228, 187, 604/195, 198, 263

[56] References Cited

U.S. PATENT DOCUMENTS

| | | | |
|---|---|---|---|
| 4,270,536 | 6/1981 | Lemelson | 604/110 |
| 4,710,170 | 12/1987 | Haber et al. | 604/195 |
| 4,775,363 | 10/1988 | Sandsdalen | 604/110 |
| 4,775,364 | 10/1988 | Alles | 604/110 |
| 4,863,427 | 9/1989 | Cocchi | 604/218 X |
| 4,923,443 | 5/1990 | Greenwood et al. | |
| 4,950,240 | 8/1990 | Greenwood et al. | 604/228 X |
| 4,961,541 | 10/1990 | Hashimoto | |
| 4,965,426 | 10/1990 | Colombo | |
| 5,000,736 | 3/1991 | Kaufhold, Jr. et al. | |

FOREIGN PATENT DOCUMENTS

| | | |
|---|---|---|
| 0278493 | 10/1988 | European Pat. Off. |
| 2613230 | 10/1988 | France |
| WO89/08468 | 9/1989 | PCT Int'l Appl. |
| WO90/03197 | 4/1990 | PCT Int'l Appl. |
| WO91/03269 | 3/1991 | PCT Int'l Appl. |
| 2214082A | 8/1989 | United Kingdom |
| 2217991A | 11/1989 | United Kingdom |

Primary Examiner—John D. Yasko
Attorney, Agent, or Firm—Charles D. Gunter, Jr.

[57] ABSTRACT

A syringe has a piston member which slides in a piston bore. The piston member is driven into the bore using a plunger so as to discharge a substance in the syringe through a needle. The plunger is connected to the piston member by a one use connection which breaks when the syringe has been completely discharged or if an attempt is made to reuse the syringe. The plunger also provides a receptacle for receiving and containing the syringe needle when this has been detached from the syringe end, after use.

7 Claims, 3 Drawing Sheets

SYRINGE

The present invention relates to a syringe, notably to a safety syringe in which the syringe plunger and needle are rendered inoperative after use of the syringe.

BACKGROUND TO THE INVENTION:

Syringes typically comprise a tubular body within which a piston head is moved axially by means of a plunger so as to dispense the contents of the space within the body ahead of the piston via a needle which is inserted into or under the skin of a person. Many forms of syringe are known, but they all have these general features and the term syringe will be used hereinafter to denote a dispensing device of this type.

Once a syringe has been used to draw blood from a patient or to administer a medicament or other material to a patient, problems arise in the disposal of the used syringe. Whilst the syringe can be constructed so that it can be disassembled and the individual components cleaned and sterilised for subsequent re-use, this is time consuming and costly. It is therefore the common practice to dispose of the used syringe to waste, for example into a strong plastic container which is disposed of by incineration or burial. However, in handling the used syringe there is the risk that the handler may accidentally jab himself with the exposed end of the needle prior to or during insertion into the disposal container. Furthermore, the syringe is disposed of in an operative condition so that it can be retrieved from the disposal container for unauthorised use, for example to inject drugs or the like.

In order to reduce the risk of accidental jabbing with the used needle, it has been proposed to apply a sheath to the needle. However, this retains the axial length of the syringe and needle, which gives problems in the space the syringe occupies in the disposal container. It has therefore been proposed to break the needle off the syringe, for example using a cutter or the like. However, this leaves a sharp needle stump projecting from the end of the syringe which can snag or stab the skin of a user. In British Specification No 2 314 082 it has been proposed that the needle sheath should be used to break the needle away from the end of the syringe at its mounting so as to render the syringe inoperative by removal of the needle. However, in applying the sheath axially over the exposed needle, the user still runs the risk that he will jab himself with the needle. Furthermore, the syringe is still operative and the needle can be replaced.

It has been proposed in U.S. Pat. No. 4,923,443 to form the plunger with a one use construction so that the plunger can be rendered inoperative once the syringe has been used. Although the syringe is now inoperative, the problems of accidental jabbing with the needle and possible re-use of the needle remain.

The need continues for a simple and effective means for rendering a syringe inoperative and for reducing the risk of accidental damage from the needle.

I have now devised a means by which a syringe can be rendered inoperative at the same time as providing a simple means for disposing of the needle which overcomes the problem of handling and disposing of a sharp object.

SUMMARY OF THE INVENTION

Accordingly, the present invention provides a syringe comprising a body portion having an axial piston bore therein and slideably journalled for axial movement therein a piston member, a plunger adapted to engage the piston for movement thereof in the piston bore, and a needle through which the contents of the body are to be discharged upon movement of the piston member, characterised in that: a. the plunger is provided with a one use connection between the operative end thereof and the piston member; b. the needle is mounted upon the hollow body by a breakable or demountable member whereby the needle can be detached from the syringe body; and in that the syringe is provided with a needle receiving member having a needle receiving chamber and incorporating means for demounting the needle from the syringe body.

Preferably, the one use connection between the plunger and the piston is provided by a member which provides a positive connection on the forward or discharge stroke of the plunger, but which can be broken or ruptured when the plunger is withdrawn so that the plunger cannot withdraw the piston member axially from the hollow body, thus preventing re-assembly of the plunger and re-use of the syringe.

Preferably, the needle is mounted on the syringe by means of a weakened mounting which is readily broken by transverse flexing of the needle whereby the whole of the needle is detached from the syringe. Alternatively, the needle is mounted by means of a detachable mounting, for example a screw or push fit mounting, and the needle receiving means incorporates means for moving the needle with respect to the syringe body, for example to unscrew or lift the needle mounting, so as to separate the needle from the syringe body during or after the needle is inserted into the needle receiving chamber.

Preferably, the needle receiving means is provided by an axially elongated hollow member which has a side, axial needle entry port whereby the user moves the needle laterally with respect to the receiving means when inserting the needle into the receiving means, thus reducing the risk of jabbing himself axially with the needle tip. Where the needle is to be detached by transverse and/or axial movement of the needle mounting with respect to the syringe body, the needle receiving means comprises an axially elongated hollow member having an axial needle entry port and means for engaging the needle mounting so as to move the mounting relative to the syringe body. Preferably, the needle mounting has one or more radial projections which engage with one or more ramp members as the needle receiving means engages the needle whereby the needle is moved axially off the syringe body.

In a particularly preferred construction, when the one use connection in the plunger shaft is broken, the residue of the plunger shaft can be removed to act as the needle receiving means. In this case the shaft of the plunger is provided with an axial bore therein which is to receive the needle and the plunger and/or the syringe body is provided with locking means whereby, when the plunger shaft containing the needle is re-inserted into the piston bore, the plunger shaft is retained with the piston bore. In such a construction, the syringe is rendered inoperative by destruction of the plunger shaft and removal of the needle, and the inoperative syringe is reduced to an axially foreshortened construction for disposal with the needle safely sheathed within the plunger body. If desired, the needle can be broken off or detached using a needle sheath which is then inserted into a suitably shaped bore in the plunger body.

The syringe of the invention can readily be manufactured by simple modification of the plunger as used in a conventional syringe so as to provide the one use connection and the bore in the plunger to receive the needle. Thus, the syringe body will typically be made from a plastic moulding having the needle extending axially therefrom and secured to the syringe body by a detachable or breakable mounting. Whilst the breakable mounting can be achieved by providing the needle receiving means with a metal or other strong rim against which a conventionally mounted needle bears as it is flexed to cause breakage of the needle, it is preferred to incorporate a break line in the plastic moulding which forms the mounting of the needle. Thus, the mounting can be formed with a circumferential score or thinning in the wall of the mounting so that the needle can be detached as a whole from the syringe.

Where the needle is to be demountably mounted on the syringe body, this can be achieved by way of a push fit, screw or other mounting which is engaged by the needle receiving means. If desired, the mounting can incorporate a breakable element as described above. Preferably, the mounting is a push fit of a needle support block upon the outlet to the syringe body so that the needle as a whole is detached from the syringe body. Preferably, the support block incorporates one or more radial projections or grooves which engage with the needle receiving means in a camming or ramp type of action whereby the needle is progressively detached axially or radially from the syringe as the needle is engaged with the needle receiving means.

The plunger for the syringe incorporates a one use connection with the piston of the syringe. The piston can be formed integrally with the shaft of the plunger and the one use connection achieved by weakening the shaft of the plunger so that it breaks upon completion of the forward, delivery stroke of the plunger. Alternatively, the one way connection can be disconnected as the plunger is withdrawn from the syringe. Many forms of one way connection may be employed, see for example those described in U.S. Pat. No. 4,923,443. However, it is particularly preferred that the connection be one which enables an axial shortening of the plunger shaft to be achieved when the residual plunger shaft is re-inserted into the piston bore as described below. Thus, it is preferred that the shaft of the plunger be partially cut away at the one use connection so that when the connection is broken crenellated, cusped or other cooperating shaped ends to the two parts of the shaft are formed. When one part is rotated relative to the other, the crowns of one part are brought into register with the troughs of the other so that the shaft shortens axially.

The needle receiving means can take a wide range of forms of hollow body into which the length of the needle can be inserted so that the needle is sheathed and the user protected from the sharp end of the needle. The receiving means typically takes the form of an axially elongated housing having either a side port extending for the length of the needle through which the needle is inserted sideways; or a terminal port through which the needle is inserted axially. Where the needle is inserted axially, it is preferred that the entry port be belled or otherwise widened so that it presents a large target for the user to insert the free end of the needle into. Typically, the belled mouth will present an opening whose cross-section diameter is from 2 to 20 times that of the external diameter of the needle itself, but which progressively reduces to approximately the external diameter of the needle so that the needle once inserted is a close fit within the housing.

The housing can be provided as a separate component, for example as the needle sheath normally provided with the syringe to protect the needle and user from damage prior to use of the syringe. However, it is preferred that the sheath incorporate means which positively engage the needle or its mounting so that once inserted into the housing the needle cannot readily be removed. For example, where the needle mounting incorporates a circumferential groove to provide the break point in the mounting, the needle sleeve can have an internal rib which engages that groove to retain the needle in the sleeve once it has been broken away from the syringe. Where the needle is a push fit on the syringe body, the needle sleeve can carry an internal lug or ramp which acts upon a radially extending flange on the needle mounting or a shoulder at the base of the mounting to lift the needle off the syringe, for example by a twisting action, as the needle sleeve is brought into axial register with the needle.

However, it is particularly preferred that he plunger shaft be formed with an internal bore which accommodates the needle as described above for the needle sleeve, and that this portion of the plunger shaft be withdrawn from the syringe when the one use connection with the piston is broken. In this way, the residue of the plunger shaft can be used to demount and house the needle in the same manner as described above for the needle sleeve. The bore within the plunger shaft can extend from the distal end of the plunger, i.e. that end which the user presses upon to depress the plunger, or can extend from the end face exposed when the one use connection is broken.

It is also preferred that the plunger shaft be provided with a snap rim, ratchet or other one way travel means for engaging the wall or lip of the piston bore in the syringe body, whereby the plunger shaft is retained within the piston bore when it is re-inserted. Due to the axial foreshortening of the plunger shaft, the residue of the plunger shaft can be depressed into the piston bore so that little on none of the lateral face of the plunger shaft is exposed, thus rendering it more difficult to remove of the residue of the plunger shaft once it has been re-inserted into the piston bore.

DESCRIPTION OF THE DRAWINGS

To aid understanding of the invention, it will now be described by way of illustration only with respect to preferred forms thereof as shown in the accompanying drawings in which.

DESCRIPTION OF THE PREFERRED EMBODIMENTS

Figure 2:
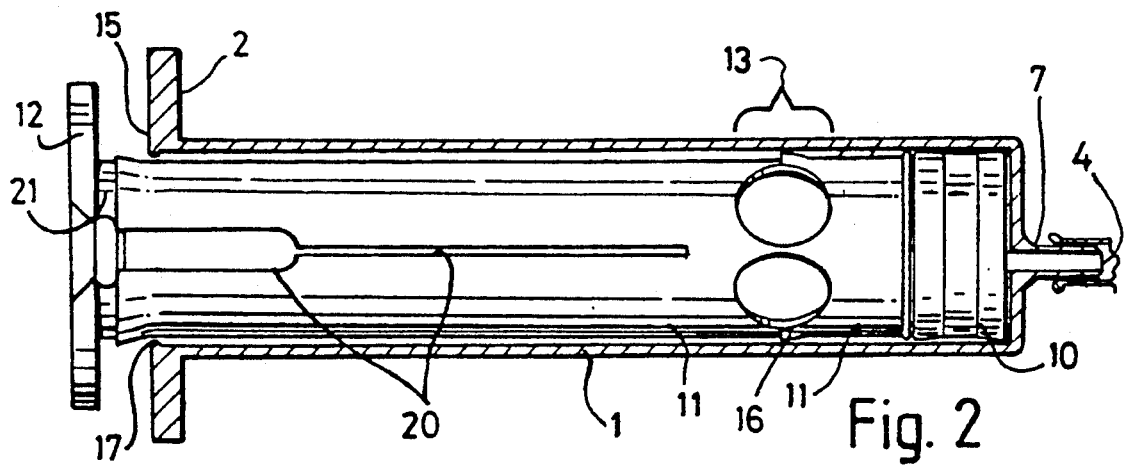
FIGS. 2 and 3 are axial cross-sectional views through a syringe incorporating the plunger and piston of FIG. 1.
Figure 4:
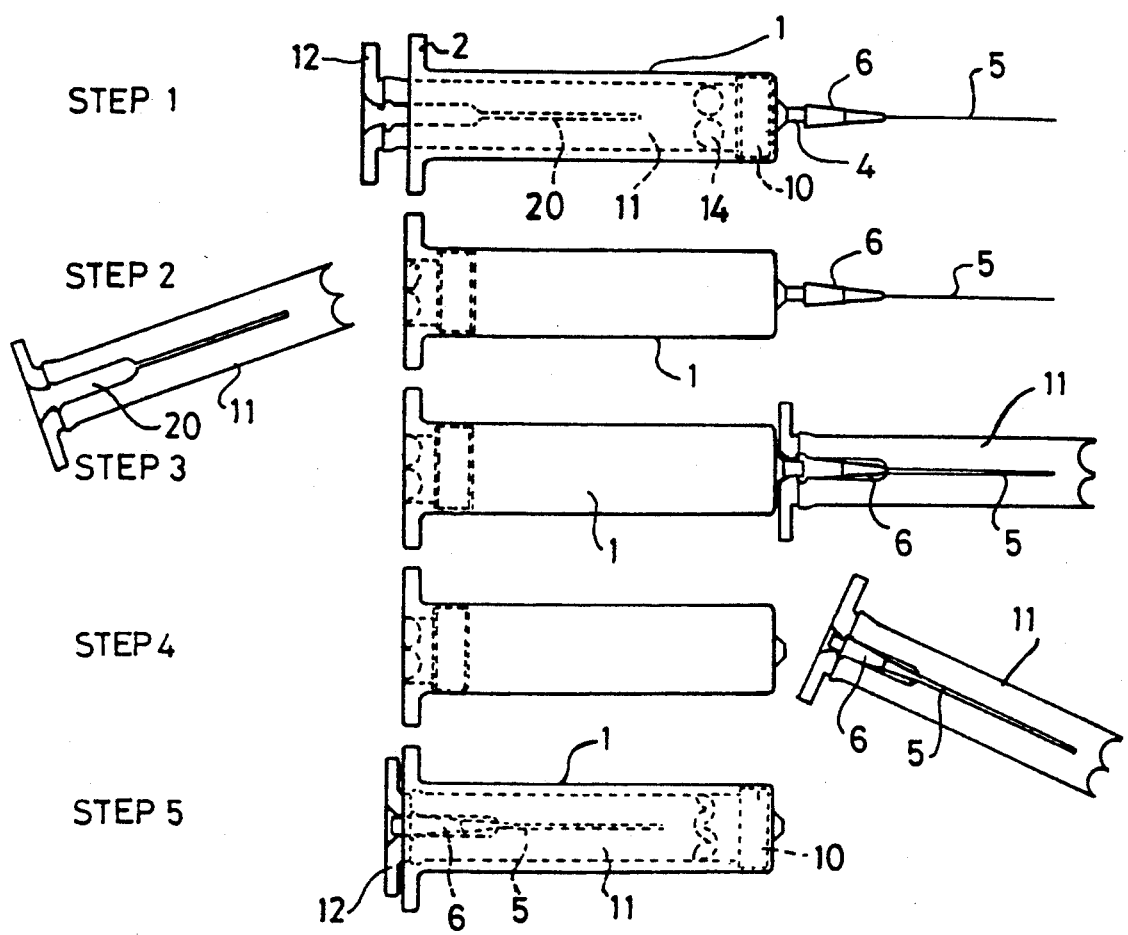
FIG. 4 shows in diagrammatic side views five stages in the operation of the syringe of FIGS. 2 and 3.
Figure 5A:
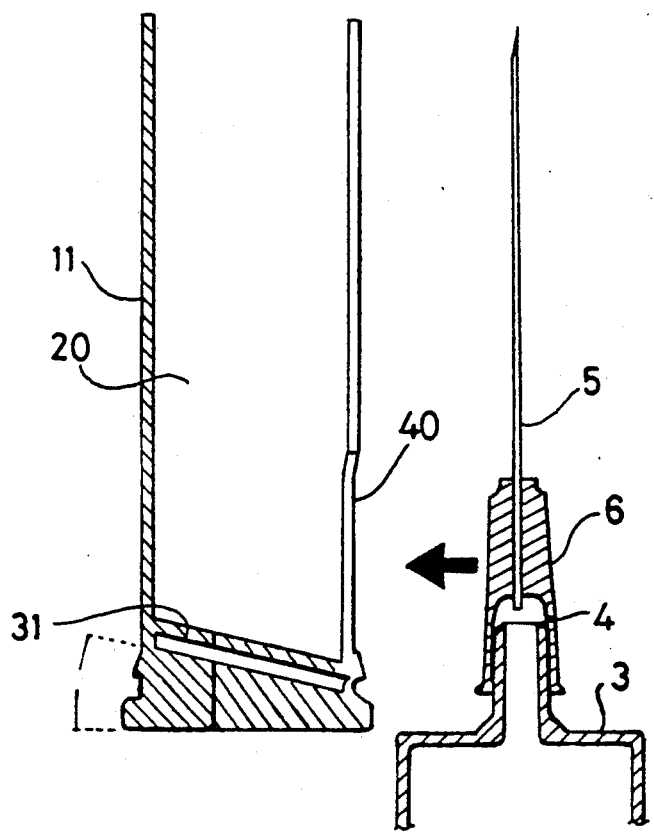
FIGS. 5a, 5b show in axial cross-section the operation of an alternative form of needle mounting.
Figure 5B:
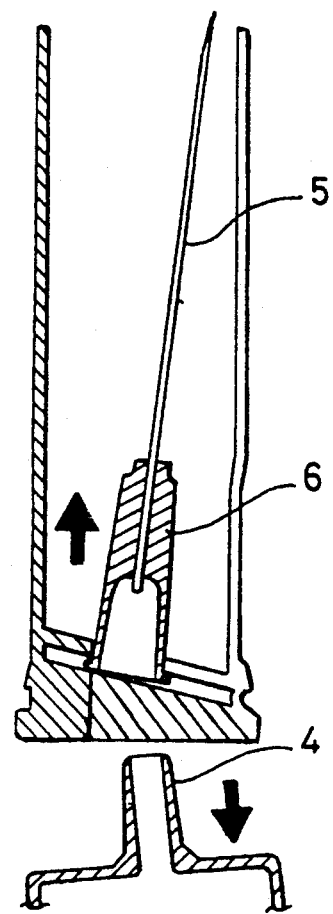

As shown in FIG. 2, the syringe comprises a generally cylindrical tubular body 1 having radial finger grip projections 2 at the open end thereof, the other end of the piston bore within the body being closed by a cross-end wall 3 having an axial outlet spigot 4 upon which is mounted a hypodermic needle 5. As shown in FIGS. 4 and 5a, 5b the needle can be mounted as a push fit upon spigot 4 by means of a needle mounting 6; or as shown in FIG. 2 can be moulded into the spigot 4 during manufacture of the syringe. In this latter case, the spigot 4 or the needle mounting block can be formed with a circumferential score or groove 7 to provide a ring of weakness at which the needle 6 can be broken away from the syringe.

Within the piston bore of the syringe body is slideably journalled a piston 10 which is driven axially by a plunger 11 which in normal use extends beyond the open end of the body 1 to provide a radially enlarged push head 12. The plunger is provided at or adjacent the piston 10 with a one time use connection 13. This can be a rupturable connection which is broken when the piston butts against the end wall 3 and pressure is applied to the connection as the push head is depressed further. A particularly preferred form of one use connection is provided by means of a series of radial bores or cuts outs 14 through the plunger shaft adjacent the piston which provide a weak point in the shaft at which the shaft can be broken by flexing the shaft. For example, the piston end of the plunger shaft can be formed with an axial recess so that the wall thickness of the shaft is reduced at this end, and the transverse bores or cut-outs 14 formed in this thinner wall area of the shaft. When the plunger shaft is withdrawn to bring the cut-outs 14 into register with the lip 15 at the open end of the piston bore, the lip provides a fulcrum against which the shaft can be flexed to break the shaft at the area of the cut-outs 14.

Figure 1:
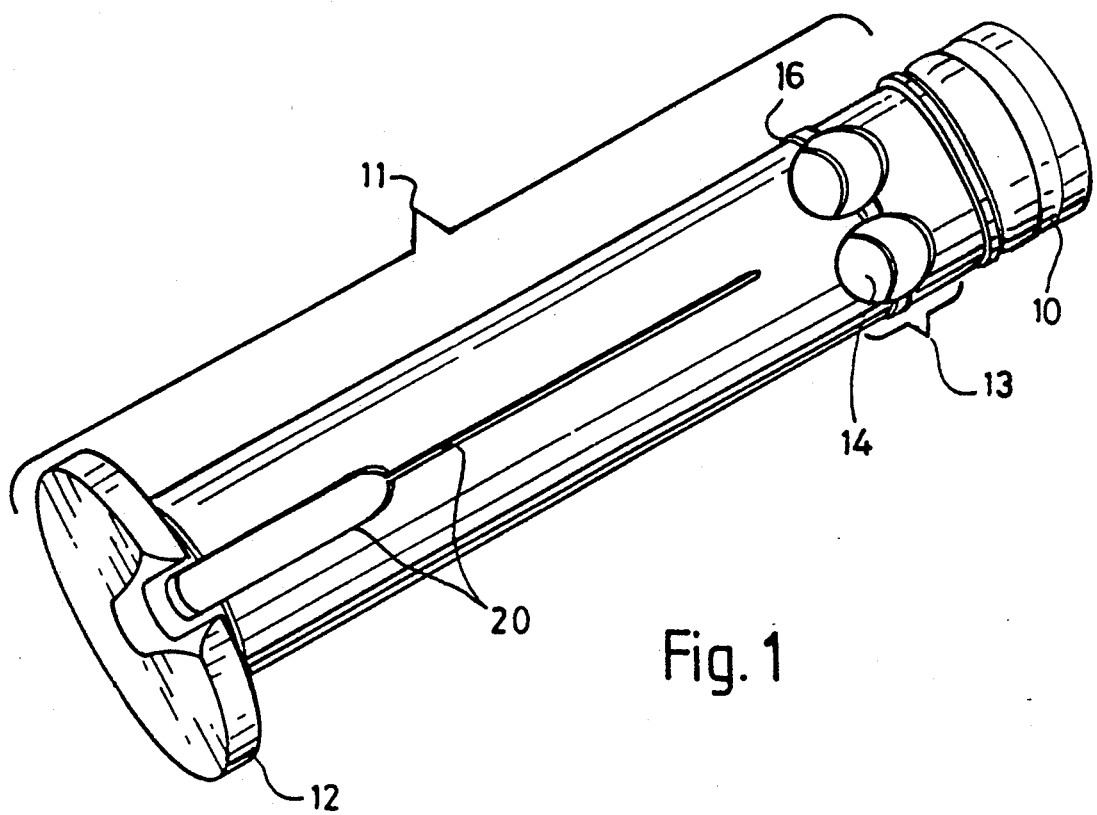
FIG. 1 is a diagrammatic perspective view of the plunger and piston for use in the syringe.
Figure 3:
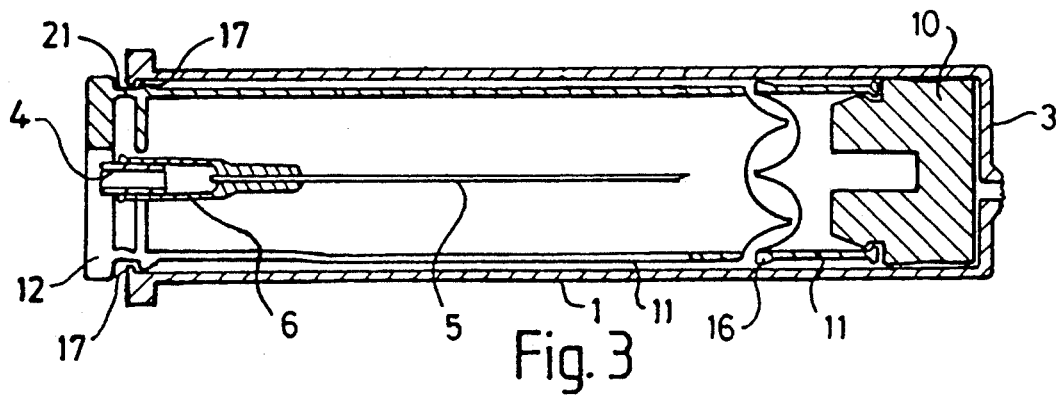

It is preferred that the wall of the plunger shaft 11 and/or the lip 15 of the piston bore be provided with means whereby the piston 10 cannot be withdrawn from the piston bore. As shown in FIGS. 1, 2 and 3, this means can be provided by a radially outward projection 16 on the plunger shaft 11 at the desired point of shaft breakage which engages an inwardly projecting circumferential shoulder or rib or a series of stops 17. In order to provide a continuous fulcrum against which to flex the shaft 11, it is preferred that the shoulder or rib 17 extend around the whole circumference of the lip 15 of the piston bore.

The plunger shaft preferably also acts as the receptacle for the needle 5 as it is detached from the syringe body. Thus, as shown in FIGS. 1, 2 and 3, the plunger shaft 11 is provided with an axial bore 20 which is dimensioned and configured so that the needle 5 and its mounting 6 are a push fit within the bore. Where the needle 5 is to be inserted axially into the bore 20, it is preferred that the mouth of the bore 20 be belled to aid insertion of the tip of the needle into the bore. Where present, the push head 12 will provided added protection to a user against contact with the tip of the needle. It is preferred that the plunger shaft 11 carry an external circumferential groove 21 or other recess which will engage with the rib 17 at the lip of the piston bore as described below.

For use, the syringe is assembled by mounting the needle 5 upon the syringe body and inserting the plunger 11 and piston 10 into the piston bore in the syringe body—step 1 in FIG. 4. Apart from the cut-outs 14 and the bore 20 in the plunger shaft 11, the syringe can be of conventional design and construction.

In use, the piston 11 is withdrawn to suck medicament or other fluid into the piston bore in the conventional manner. The fluid is injected in the conventional manner by depressing the push head 12 to drive the piston 10 axially. After use, the plunger shaft 11 is broken by withdrawing the plunger until the projections 16 on the shaft 11 engage the rib 17 at the lip of the piston bore. The shaft is then flexed laterally to cause it to break at the ring of weakness introduced by the cut-outs 14—step 2 in FIG. 4.

The residue of the shaft 11 is then inverted and the needle 5 is inserted into the bore 20—step 3 in FIG. 4. The bore 20 can have an internal bead or groove 22 which engages with a corresponding groove or bead in the needle mount 6 or the spigot 4 when the needle 5 is pushed fully home in bore 20 in the shaft 11. The shaft 11 is then flexed about the longitudinal axis of the needle to cause the needle and its mount to break away from the syringe body—step 4 in FIG. 4. By virtue of the engagement of the beads and grooves in the bore 20 and the needle or its mounting, the needle is firmly retained within bore 20.

The shaft 11 is then inverted against and re-inserted into the piston bore of the syringe body 1. By aligning the remnants of the cut-outs 14 with one another so that the axially projecting portions 23 are out of alignment with one another, the axial length of the shaft 11 can be reduced to allow the rib 17 at the lip of the piston bore to engage in the groove 21 in the plunger shaft and thus lock the shaft within the piston bore—step 5 in FIG. 4. In this way, the syringe provides its own needle breaker and receptacle means, which aids the safe disposal of the needle and syringe, as well as rendering the syringe inoperative by breaking the plunger shaft.

In the alternative construction shown in FIGS. 5a, 5b the needle 5 is mounted as a push fit upon the spigot outlet 4 to the syringe body 1. The plunger shaft 11 has an axial needle entry port 30 in the side wall of the shaft in place of the entry in the end face thereof as shown in FIG. 1. The entry port 30 feeds the needle radially into the axial bore 20 within the shaft 11. The end face of the shaft can be closed as shown, in which case the plunger shaft can be of a hollow tubular construction with the central bore providing the needle receiving chamber 20. At the foot of the chamber 20 is provided a transverse ramp 31 which engages with the foot of the needle mount 6 or a radial projection carried by the mount 6. As the needle enters the chamber 20, the ramp 31 engages the needle mount and lifts it axially off the spigot 4—as shown in Figure b of FIG. 5. If desired, the plunger shaft 11 can be tilted to assist lifting of the needle 5 clear of the spigot. The needle is retained in the chamber 20 and the plunger shaft 11 can then be inserted into the syringe body as in step 5 described above with respect to FIG. 4.

I claim:

1. A safety syringe comprising:

a body portion having an axial piston bore therein;

a piston member journalled within the piston bore for axial movement within the bore;

a plunger member having a first end for actuation by a user and a second end adapted to engage the piston member for movement of the piston member in the piston bore;

a one use connection located at or adjacent said second end of said plunger member, said one use connection being such as to enable the movement of the piston member to be disabled upon disconnection of said one use connection, the one use connection further being such that an axial shortening of the plunger member can be achieved after the one use connection has been disconnected, whereby the plunger member can be substantially completely inserted into the piston bore to reduce access by the user to said first end of the plunger member; and wherein the one use connection is provided by a circumferential line of weakness at which the one use connection can be broken to disable the piston member, which line is configured so as to provide axially opposed residues of the one use connection which can be inter-engaged to achieve the axial shortening of the plunger member.

2. A safety syringe as claimed in claim 1, wherein a needle is mounted upon the body portion through which a substance contained in the piston bore is to be discharged upon movement of the piston member.

3. A syringe as claimed in claim 2, wherein the needle is mounted upon the said body portion by a breakable or demountable member whereby the needle can be detached from the syringe body, and a needle receiving member is provided having a needle receiving chamber and incorporating means for detaching the needle from the body portion.

4. A safety syringe as claimed in claim 1, wherein the line of weakness in said plunger member is provided by partially cutting away the plunger member at the one use connection.

5. A safety syringe as claimed in claim 3, wherein the said plunger member provides said needle receiving member, whereby after disconnection of the said one use connection the said plunger can be withdrawn from the piston bore, the needle separated from the syringe body and inserted into the needle receiving chamber in the plunger member and the plunger member re-inserted into the piston bore to retain the needle within the piston bore.

6. A safety syringe as claimed in claim 3, wherein the needle receiving means is provided by an axially elongated hollow member which has a side, axial needle entry port, through which the needle can be inserted at least transversely.

7. A safety syringe as claimed in claim 5, wherein the needle receiving means is provided by an axially elongated hollow member which has a side, axial needle entry port, through which the needle can be inserted at least transversely.

* * * * *